Dec. 3, 1968 P. MERCURI ET AL Plant Pat. 2,848
CARNATION PLANT
Filed March 11, 1966
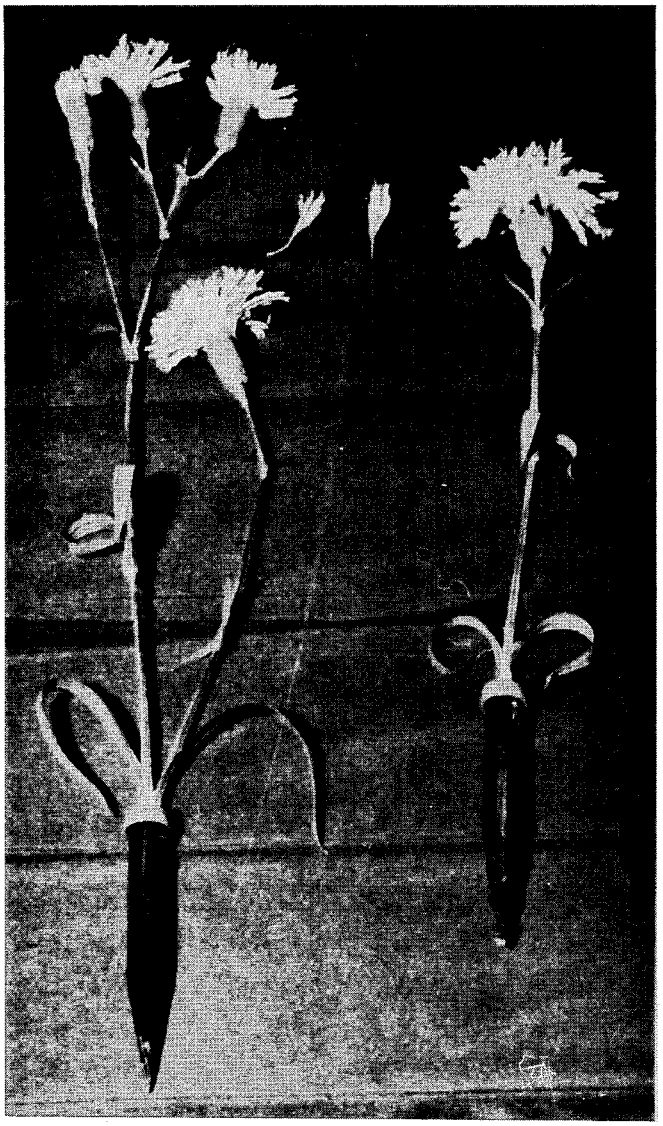
Inventor
PASQUALE MERCURI
GEORGE MERCURY
By Paul H. Craig, Jr.
Attorney United States Patent Office Plant Pat. 2,848
Patented Dec. 3, 1968

2,848
CARNATION PLANT

Pasquale Mercuri, 189 Post Road, and George Mercury, 260 Landham Road, both of Sudbury, Mass. 01776

Filed Mar. 11, 1966, Ser. No. 533,732
1 Claim. (Cl. Plt.—70)

The present invention relates to a new and distinct variety of carnation plant, which is characterized particularly by a quilled petal structure. The term, "quilled petal structure," as used herein means a petal structure having a series of ridges formed by folds of the petal which extends from the outer edge of the petal inwardly substantially to the point of attachment of the petal.

We discovered this invention as a mutation of the unpatented commercial carnation variety, "S. Arther Peterson," which was being grown commercially by us and which was derived through mutations of the variety disclosed in Plant Patent No. 699, issued Jan. 15, 1946, to Wm. Sim.

The original reproduction by cuttings was carried out by us in our greenhouses at Sudbury, Mass., and these cuttings reproduced the variety true to form.

This invention may be grown as a "standard" (single bloom per stalk) or as a "miniature" (multiple bloom per stalk) with the usual commercial growing methods.

The accompanying drawing shows miniature blooms on the stalk on the left and a standard bloom on the stalk on the right with the detached petals showing the "quilled petal structure" between the two stalks.

The coloring of the specimens shown only in black and white in this accompanying drawing, which corresponds to that of the parent, consists of red and white stripes extending from the outer petal edge inward toward the point of attachment.

The following is a detailed description of our invention in accordance with Ridgeway's Color Standards and Nomenclature:

Parent: S. Arther Peterson.

Blooming season: Starts blooming the first year from cuttings and blooms year round.

Flowers:

*Color.*—White with red stripes of carmine Plate No. I-*i*-1 extending from outer petal edge inward substantially to the point of attachment of the petal.

*Petalage.*—Double.

Foliage:

*Color.*—Generally green to bluish green Plate XVIII-*i*-33′, winter green to Plate XIX-*x*-39′ dark cinnabar green with the more recently sprouted portions a lighter shade of green.

*Size.*—The size of the flowers and foliage is the same as commercial carnation varieties for both "standards" and "miniatures."

We claim:

1. A new and distinct variety of carnation plant as herein disclosed, characterized as to novelty by a quilled petal structure.

No references cited.

ROBERT E. BAGWILL, *Primary Examiner.*